(12) United States Patent
Donaldson

(10) Patent No.: US 10,178,949 B2
(45) Date of Patent: Jan. 15, 2019

(54) METHOD, SOFTWARE AND APPARATUS FOR TESTING A PATIENT'S VISUAL FIELD

(71) Applicant: IbisVision Limited, Aberdeen (GB)

(72) Inventor: Blair Donaldson, Aberdeen (GB)

(73) Assignee: IbisVision Limited, Aberdeen (GB)

( * ) Notice: Subject to any disclaimer, the term of this patent is extended or adjusted under 35 U.S.C. 154(b) by 107 days.

(21) Appl. No.: 15/515,616

(22) PCT Filed: Sep. 23, 2015

(86) PCT No.: PCT/GB2015/052759
§ 371 (c)(1),
(2) Date: Mar. 30, 2017

(87) PCT Pub. No.: WO2016/051136
PCT Pub. Date: Apr. 7, 2016

(65) Prior Publication Data
US 2017/0245753 A1 Aug. 31, 2017

(30) Foreign Application Priority Data
Sep. 30, 2014 (GB) .................................. 1417208.4

(51) Int. Cl.
*A61B 3/024* (2006.01)
*A61B 3/113* (2006.01)
(Continued)

(52) U.S. Cl.
CPC ............ *A61B 3/024* (2013.01); *A61B 3/0091* (2013.01); *A61B 3/113* (2013.01); *G06F 3/013* (2013.01)

(58) Field of Classification Search
CPC ........ A61B 3/024; A61B 3/113; A61B 3/0041; A61B 3/14; A61B 3/025; A61B 3/0025; A61B 3/0033; A61B 3/0058
(Continued)

(56) References Cited

U.S. PATENT DOCUMENTS 6,290,357 B1   9/2001   Massengill
6,367,932 B1   4/2002   Donaldson
(Continued)

FOREIGN PATENT DOCUMENTS

CN   1827035     9/2006
CN   103501688   1/2014
(Continued)

*Primary Examiner* — Collin X Beatty
(74) *Attorney, Agent, or Firm* — Dorton and Willis LLP; Ryan Willis

(57) ABSTRACT

A method for testing a patient's (2) visual field using testing apparatus. A fixation target is provided on a display (3) at a known target position and the patient's (2) direction of gaze is tracked using an eye tracker to determine the patient's point of regard. A marker (5) is provided on the display (3) indicating the patient's (2) point of regard, where the marker (5) moves with movement of the patient's (2) point of regard. It is detected when the marker (5) is moved to the fixation target and a new target is then provided on the display at a further known target position. The new target is recorded as detected if the marker (5) is moved to the new target, with the new target then becoming the fixation target. The steps are repeated for further new targets for determining the patient's (2) visual field based on the positions of the new targets that have been detected.

20 Claims, 1 Drawing Sheet

Figure 1:
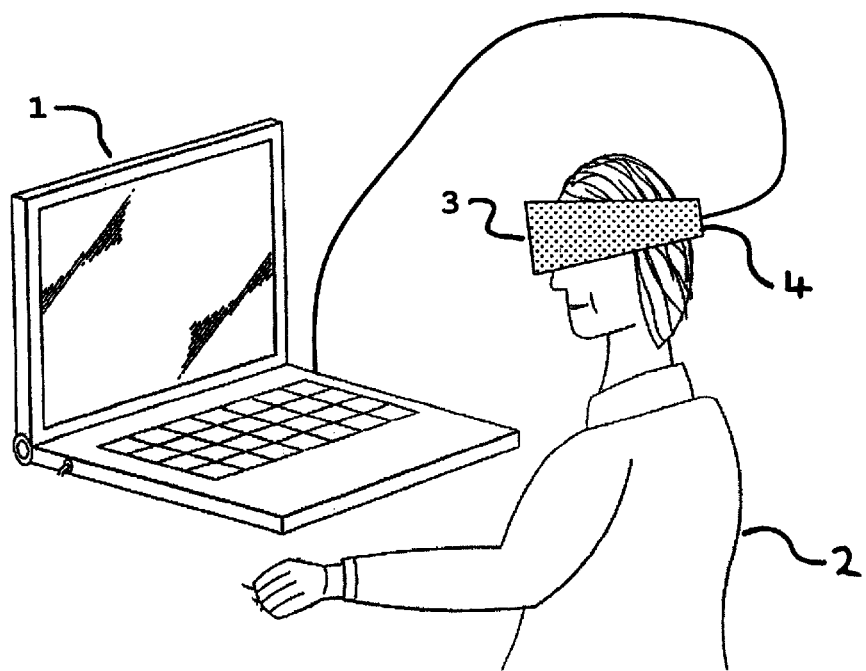

(51) Int. Cl.
*G06F 3/01* (2006.01)
*A61B 3/00* (2006.01)

(58) Field of Classification Search
USPC .................. 351/209, 224–226, 237, 246
See application file for complete search history.

(56) References Cited

U.S. PATENT DOCUMENTS

| 8,937,591 | B2 * | 1/2015 | Julian | ............... G06F 3/04812 |
| | | | | 345/156 |
| 9,164,583 | B2 | 10/2015 | Williams | |
| 2013/0044290 | A1 | 2/2013 | Kawamura | |
| 2014/0218691 | A1 | 8/2014 | Pela | |

FOREIGN PATENT DOCUMENTS

| CN | 103815866 | 5/2014 |
| CN | 201580065142.9 | 6/2018 |
| JP | 2003000542 | 1/2003 |
| WO | PCT/GB15/52759 | 2/2016 |

* cited by examiner

METHOD, SOFTWARE AND APPARATUS FOR TESTING A PATIENT'S VISUAL FIELD

The present invention relates to a method, apparatus and software for use in testing a patient's visual field.

Visual field tests are examinations conducted in order to determine the extent of a patient's visual field. There are a number of existing tests for measuring and generating a graphical representation of a patient's visual field, such as for example the Bjerrum test, the Static Perimetry test and the Optokinetic test. Problems associated with known tests stem from the fact that in each case the patient is required to give some sort of indication or response as to when they see the target in their visual field. The exact point of when the target is seen can be somewhat subjective and unclear and can therefore lead to significant inaccuracies. Moreover, patients can often lose fixation or concentration, leading them to scan the screen for the next target, which leads to an inaccurate picture of what is detected as within their peripheral visual field.

An object of the present invention is to seek to overcome the problems associated with such known tests and apparatus.

According to a first aspect of the present invention, there is provided a method for testing a patient's visual field using testing apparatus, the method comprising the steps of: (a) providing a fixation target on a display at a known target position; (b) tracking the patient's direction of gaze using an eye tracker to determine the patient's point of regard on the display; (c) providing a marker on the display indicating the patient's point of regard, where the marker moves with movement of the patient's point of regard; (d) detecting when the marker is moved to the fixation target; (e) once the marker is moved to the fixation target, providing a new target on the display at a further known target position; (f) recording the new target as detected if the marker is moved to the new target, the new target then becoming the fixation target; (g) repeating steps (e) and (f) for further new targets at further known target positions for determining the patient's visual field based on the positions of the new targets that have been detected.

With such a method, the fixation target is a target over which the patient is initially encouraged to focus on. The new target is a visual field target provided somewhere on the screen in what would be the visual field of a normal patient. If the patient is aware of the visual field target while looking at the fixation target, then they are encouraged to move their focus to it. The visual field target then becomes the fixation target at a revised known target position. A new visual field target can then be provided on the display and the process is repeated to build up a visual field.

In this way, with the present invention, the patient's point of regard on the display screen is accurately determined using eye tracking, thereby ensuring that focus on the fixation target has been maintained at the point when a new target was presented in the patient's peripheral field. At the same time, the provision of the marker indicating the patient's current point of regard provides a synergetic effect in that the patent is provided with something on screen to focus on and control relative to the current fixation target. That is, the marker functions as a target sight for targets, introducing a gaming element to the testing process which helps to maintain the patient's concentration. As such, the patient's gaze is less likely to deviate from the current fixation target since this would cause the marker to move off the fixation target, prompting the patient to move their focus back.

Conveniently, step (f) further comprises recording the new target as not detected if, after a period of time, the marker is not moved to the new target.

Conveniently, the method further comprises the step of preparing a visual field map based on the positions of targets that have been recorded as detected and not detected.

Preferably, step (f) further comprises repositioning the new target if it is recorded as not detected. In this respect, this gives the patient an opportunity to establish whether such a target is in their visual field. If the patient is not aware of such a target then it is repositioned, for example closer to the fixation target, to try to establish the limits of the patient's visual field at that orientation.

Preferably, the new target is repositioned in incremental steps. This helps to provide time for the patient to react.

Preferably, the marker is displayed as one of a dot, a circle, or crosshairs. In this way, the marker appears as a target sight for new field targets, helping to reinforce the gaming elements to the testing process.

Conveniently, step (f) further comprises providing a visual or audible notification to the patient when the marker is moved to the new target. Preferably, the visual or audible notification to the patient is continuous while the marker is in contact with the new target. In this way, if the patient's point of regard deviates from the current fixation target, they are prompted to move their focus back to the fixation target by the change or lack of visual or audible notification. Alternatively, an alert may sound or display if the patient's point of regard moves off from the fixation target once on it. Again, this helps to prompt the patient to move their focus back to the fixation target.

Conveniently, step (f) further comprises removing the previous fixation target from display after the marker is moved to the new target.

Conveniently, step (f) further comprises determining if the marker is moved along a path between the fixation target and the new target. Preferably, the path has a width for providing a tolerance to inaccuracy in the patient's movement of their direction of gaze. In this way, a notional direct linear path between the fixation target and the new target is used to define a wider path or channel that is designated as being a region in which the marker is determined as travelling directly to the newly presented visual field target with an acceptable or reasonable degree of tolerance to allow for inaccuracies in the patient's movement of their direction of gaze or in the eye tracking system.

Preferably, step (f) further comprises removing the new target from display if the marker is moved outside of the path. In this way, the patient is prevented from scanning the display screen looking for new targets.

Preferably, if the new target is removed from display, a notification is generated to prompt the patient to move their point of regard back to the fixation target.

Preferably, the method further comprises conducting a calibration procedure, the calibration procedure comprising the steps of: providing a calibration fixation target on the display; prompting the patient to focus on the calibration fixation target for a period of time; adjusting the position of the marker indicating the patient's point of regard over the calibration fixation target. In this way, more accurate eye tracking is achieved.

Preferably, step (f) further comprises recording the reaction time of the patient.

Preferably, step (e) comprises changing the brightness of the new target and/or the contrast of the new target relative to the displayed background over a period of time. For example, the brightness or contrast may increase over a period of time. For instance, a visual field target may be presented by fading in and becoming progressively more visible. That is, the visual field target may start from a point where it is substantially blended with the display background, with a similar colour and brightness. The contrast with the background may then increase steadily over a period of time until the visual field target is detected or a maximum contrast or brightness is reached. More preferably, wherein step (e) further comprises recording the brightness and/or contrast level of the new target at the time of detection. The step of recording the brightness and/or contrast level of the new target at the time of detection may comprise accounting for the reaction time of the patient. With the above features an indication of a threshold level of visibility for targets may be displayed on the output results map.

Conveniently, in step (d), the new target is presented once the marker is moved at least partially over the fixation target.

Conveniently, the method further comprises moving the fixation target and moving the new target with the fixation target to maintain it at a constant position relative to the fixation target, wherein the patient is encouraged to track the movement by maintaining the marker over the fixation target and the new target is only displayed when the marker is over the fixation target or being moved directly towards the new target. Having the fixation target move ensures that the patient has to maintain their attention thereon.

The results from the method may be recorded in graphical or pictorial form, representing the visual field of the patient. The results from testing the same patient at different times or different target contrast levels may further be superimposable for indicating the deterioration/progress of the patient, as well as the severity of their defect of visual field.

Preferably, the method further comprises providing the patient with a patient actuated indicator for designating a target as detected, wherein the step of recording the target as detected comprises requiring the patient to actuate the patient actuated indicator once the marker is moved to the target. The patient's involvement in the test is thereby increased, leading to improved concentration, and consequently more accurate results. In this way, the test may be thought of as requiring the patent to both aim at each target with their point of regard marker and fire at the target using their button or trigger. In such embodiments, it is therefore also preferable that the method further comprises providing a visual or audible notification to the patient when the target is recorded as detected. More preferably, the visual notification comprises altering the appearance of the marker and/or the target. In embodiments, a different visual or audible notification may be provided to the patient if the patient actuated indicator is actuated when the marker has not been moved to the target.

According to a second aspect of the present invention, there is provided a software program having instructions for implementing a method for testing a patient's visual field using testing apparatus, the software program comprising: (a) instructions for providing a fixation target on a display at a known target position; (b) instructions for tracking the patient's direction of gaze using an eye tracker to determine the patient's point of regard on the display; (c) instructions for providing a marker on the display indicating the patient's point of regard, where the marker moves with movement of the patient's point of regard; (d) instructions for detecting when the marker is moved to the fixation target; (e) instructions for providing a new target on the display at a further known target position once the marker is moved to the fixation target; (f) instructions for recording the new target as detected if the marker is moved to the new target, the new target then becoming the fixation target; (g) instructions for repeating instructions (e) and (f) for further new targets a further known target positions for determining the patient's visual field based on the positions of the new targets that have been detected.

According to a third aspect of the present invention, there is provided apparatus for testing a patient's visual field, the apparatus comprising: a display; an eye tracker for tracking the patient's direction of gaze to determine the patient's point of regard on the display; a control unit configured to (a) present a fixation target on the display at a known target position; (b) present a marker on the display indicating the patient's point of regard, where the marker moves with movement of the patient's point of regard; and (c) present a new target on the display at a further known target position once the marker is moved to the fixation target; a memory for recording the new target as detected if the marker is moved to the new target, the new target then becoming the fixation target; wherein the control unit is further configured to present further new targets at further known target positions and the memory is for recording if the further new targets are detected for determining the patient's visual field based on the positions of the new targets that have been detected.

Preferably, the apparatus comprises a head mounted unit comprising the display and the eye tracker. By integrating the display and eye tracker within the head unit, the position of the patient's eyes relative to where the display screen is visualised is kept constant. Furthermore, this allows the present invention to be provided as a compact apparatus.

Preferably, the apparatus further comprises a patient actuated indicator for designating a target as detected, wherein the control unit is configured to record targets as detected only when the patient actuated indicator is actuated by the patient once the marker is moved to the target. Preferably, the control unit is further configured to provide a visual or audible notification to the patient when a target is recorded as detected. More preferably, the control unit is further configured to provide said visual notification by altering the appearance of the marker and/or the target. In embodiments, the control unit may be further configured to provide a different visual or audible notification to the patient if the patient actuated indicator is actuated when the marker has not been moved to the target.

According to a fourth aspect of the present invention, there is provided a method for testing a patient's visual field using testing apparatus, the method comprising the steps of: (a) providing a fixation target on a display at a known target position and providing the patient with a patient actuated indicator; (b) tracking the patient's direction of gaze using an eye tracker to determine the patient's point of regard on the display; (c) providing a marker on the display indicating the patient's point of regard, where the marker moves with movement of the patient's point of regard; (d) detecting when both the marker is moved to the fixation target and the patient actuated indicator is actuated to designate a target as detected; (e) once the target is detected, providing a new target on the display at a further known target position; (f) recording the new target as detected if the marker is moved to the new target and the patient actuated indicator is actuated, the new target then becoming the fixation target; (g) repeating steps (e) and (f) for further new targets at further known target positions for determining the patient's visual field based on the positions of the new targets that have been detected.

Figure 2:
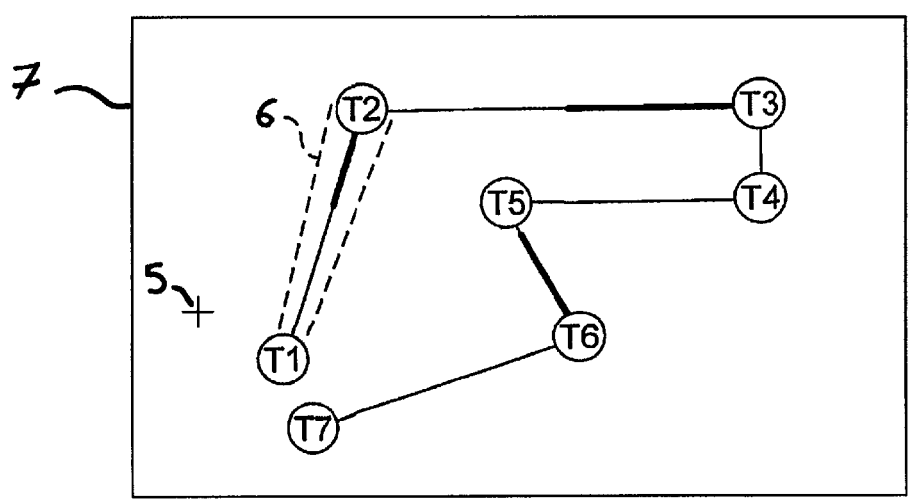

Examples of the present invention will now be described with reference to the accompanying drawings of which:

FIG. 1 shows a perspective view of apparatus for implementing an embodiment of the present invention; and FIG. 2 shows a schematic representation of a visual field test display screen for implementing a visual field test of an embodiment of the invention.

FIG. 1 shows an example of testing apparatus for implementing an embodiment of the present invention. As shown, the patient 2 is provided with a head mounted unit 4 connected to computer 1 on which is stored software with instructions for implementing the testing methodology according to this embodiment of the present invention.

Head unit 4 provides a head mounted display 3 integrated with an eye tracker for tracking the patient's direction of gaze. In this embodiment, the display 3 is a retinal display unit that projects light directly into a patient's eye or eyes such that an image of the visual field test display screen is formed on their retina. The eye tracker comprises cameras integrated into the head unit 4 and directed toward the patient's eyes. Processing within either the head unit 4 or the computer 1 utilises the feed from the integrated cameras to determine the patient's direction of gaze. By integrating the display 3 and eye tracker within the head unit 4, the position of the patient's eyes relative to where the display screen is visualised is kept constant.

In alternative embodiments of the invention, alternative displays 3 may be used. For example, more conventional head mounted displays which comprise small OLED, LED or LCD display screens may be used. The head mounted display may also be an actual flat or curved display in front of the patient's eye/s. Equally, more conventional display screens, such as computer monitors, projector systems, or flat screen displays could also be used. In such alternative embodiments, the eye tracker may be provided as a separate unit.

FIG. 2 shows a schematic representation of a visual field test screen 7 similar to that which would be visualised as being displayed on the display 3 to the patient 2 wearing the head mounted unit 4. The screen 7 has a display background on which a sequence of target spots Tn are displayed. A marker 5 is displayed in the form of crosshairs and is moveable in real time with the patent's direction of gaze under the control of the eye tracker such that the marker 5 designates the patient's point of regard on the display screen 7. As such, the position of the marker 5 provides a continuous indication of what the patient is looking at on the display screen 7.

Prior to the main visual field test, a calibration process is performed whereby a patient is prompted to focus on a displayed calibration target spot in order to calibrate the eye tracker. The patient is asked to maintain their focus on the calibration target spot for a period of time. During this time, the position of the marker 5 is adjusted so it is accurately positioned over the calibration target spot, where the patient's point of regard is located. The eye tracking processing may also compensate for minor inaccuracies in detection or small eye movements by damping the movement of the marker 5. The calibration process may be repeated later if, for example, the patient considers the position of the marker to be inaccurate.

An example of the main test will now be described with reference to FIG. 2. At the start of a test program, the first target T1 and the moveable marker 5 are displayed on display 3. The patient is prompted to begin the test by moving their point of regard, and hence marker 5, to the target T1. The patient is also instructed to move their point of regard towards any presented visual field target they subsequently see. These prompts may be from a practitioner administering the test, or be provided automatically by the software generating audio or on-screen instructions.

When the patient looks at target T1, since their direction of gaze is directed toward the target, the position of the marker 5 will coincide with target T1 on the display. The action of the marker 5 being moved over target T1 thereby designates it as the current fixation target. Establishing the marker 5 over the target can be confirmed by an audible or visual notification, such as an explosion effect. In another example of a visual notification, either or both of the marker 5 and the target T1 may change their shape or colour. The audible or visual notification may be continuous while the marker 5 remains in contact with the current fixation target in order to keep the patient focused on it.

Once it is confirmed that the patient has moved the marker 5 over target T1, target T2 is then displayed on the screen as a new visual field target. If the patient becomes aware of this new target in their visual field while still looking at target T1, they will move their direction of gaze toward it in accordance with the pre-test instructions. Once the patient is looking at the new target T2, because their point of regard will coincide with the new target, marker 5 will have moved over it. This indicates this target has been seen, which is recorded as a positive patient response for that position by computer 1. Target T2 then becomes the new fixation target. Again, establishing the marker 5 over the new target T2 can be confirmed by an audible or visual notification.

With the marker 5 over the target T2, previous fixation target T1 disappears and a new target, target T3, appears and the test repeats. The process continues on through targets T4 to T7 in a sequence to test different positions relative to the respective fixation target. As such, the positions of the presented sequence of visual field targets and associated recorded patient responses may be used to generate a visual field map. This can show regions which do not appear visible to a patient and hence help identify defects in their vision.

To help to maintain the patient's direction of gaze, the fixation target may be configured to vibrate or oscillate or otherwise change its appearance, once it has been selected by the patient directing their point of regard to it. This oscillation or movement helps to maintain the patient's direction of gaze on the target as their eyes are drawn to the movement.

In the event the marker 5 moves off the current fixation target, the test is paused until they return the marker 5. However, in order to allow the marker 5 to be moved to the next visual field target, a notional positive movement corridor or channel 6 is defined along the path between the targets. As shown by the dashed line 6 in FIG. 2, this corridor or channel 6 is wider than the marker 5, and has a width selected to allow for minor inaccuracy in the patient's direction of gaze movements. Accordingly, during the test, a patient is able to move their point of regard directly to new targets along the positive movement channel 6. However, any other movement of the marker 5 outside this positive movement channel 6 indicates the patent is scanning the display screen. This causes the test to be paused by removing the new visual field target from display. The patient must then return their point of regard back to the fixation target to recommence the test.

In the above embodiment, if a patient does not move their point of regard marker 5 to the new visual field target after a period of time, the new visual field target at that position is recorded as not seen. In this event, in embodiments, the size and/or contrast of the new visual field target may be increased over a period of time until the target is seen, and the size and/or contrast upon detection may be recorded. In alternative embodiments, if a new visual field target is not seen, it can be moved under computer control to where it is seen and the position recorded, or other targets are displayed one at a time until one is seen and the process continues further. By varying the distance and angle direction of the new visual field target in relation to the fixation target, which was the previous visual field target, a visual field can be built up. Hence, the patient simply follows targets appearing on the screen with their point of regard.

The apparatus may further comprise means for repositioning the display position of the fixation target to allow a new target to be positioned on the screen. In this respect, with certain patients, a substantial part of the field on one side may be missing such that as successive targets are presented, only those not in the missing part are seen. This could have an effect in gradually moving the fixation target further and further to one side of the display. Consequently, the useful area of the screen for presenting further targets will be diminished. To counter this, the fixation target can be moved under the control of the computer to a position where there is sufficient space left on the display to present further targets and thus continue the test. Such a means for repositioning the target may, for example, be provided in the form of software for the computer.

It will be appreciated that the present invention may be applied to many different configurations, the detailed embodiments being straightforward for those skilled in the art to implement.

In this connection, for example, in further alternative embodiments, the testing apparatus may further comprise a patient actuated indicator, such as a button or trigger that can be pressed by the patient during the test for designating targets as seen. In such embodiments, at the start of a test program, in addition to the patient being prompted to move their point of regard identified by marker 5 to each target T, the patient may also be instructed to actuate the indicator when the marker 5 is over the target to designate it as seen. This patient input would also be monitored by computer 1 such that each target is only recorded as having been seen, and the next target displayed, once both actions occur simultaneously. The patient's involvement in the test is thereby increased, leading to improved concentration, and consequently more accurate results. In this way, the test may be thought of as requiring the patent to both aim at each target with their direction of gaze marker and fire at the target using their button or trigger. In such embodiments, it is therefore also preferable to further incorporate the features of having a visual or audible notification to the patient when the marker has been designated as seen. For example, the appearance of either or both of the marker 5 and the target T may change. Equally, in embodiments, an alternative visual or audible notification may also be provided to the patient if they actuate the indicator when the marker 5 is not over the target. This alternative visual or audible notification, which may be, for instance, a "boo" sound, may thereby be used to alert the patient that they have missed the target.

In embodiments, the results of the visual field test may be output as a visual field map. Equally, the results of the test may be uploaded to a cloud storage system, for example, for comparison with other patients.

The invention claimed is:

1. A method for testing a patient's visual field using testing apparatus, the method comprising the steps of:
(a) providing a fixation target on a display at a known target position;
(b) tracking the patient's direction of gaze using an eye tracker to determine the patient's point of regard on the display;
(c) providing a marker on the display indicating the patient's point of regard, where the marker moves with movement of the patient's point of regard;
(d) detecting when the marker is moved to the fixation target;
(e) once the marker is moved to the fixation target, providing a new target on the display at a further known target position;
(f) recording the new target as detected if the marker is moved to the new target, the new target then becoming the fixation target;
(g) repeating steps (e) and (f) for further new targets at further known target positions for determining the patient's visual field based on the positions of the new targets that have been detected.

2. A method according to claim 1, wherein step (f) further comprises recording the new target as not detected if, after a period of time, the marker is not moved to the new target.

3. A method according to claim 2, further comprising the step of preparing a visual field map based on the positions of targets that have been recorded as detected and not detected.

4. A method according to claim 2, wherein step (f) further comprises repositioning the new target if it is recorded as not detected.

5. A method according to claim 4, wherein the new target is repositioned in incremental steps.

6. A method according to claim 1, wherein step (f) further comprises providing a visual or audible notification to the patient when the marker is moved to the new target.

7. A method according to claim 1, wherein step (f) further comprises determining if the marker is moved along a path between the fixation target and the new target, the path having a width for providing a tolerance to inaccuracy in the patient's movement of their direction of gaze.

8. A method according to claim 7, wherein step (f) further comprises removing the new target from display if the marker is moved outside of the path.

9. A method according to claim 8, wherein if the new target is removed from display, a notification is generated to prompt the patient to move their point of regard back to the fixation target.

10. A method according to claim 1, further comprising conducting a calibration procedure, the calibration procedure comprising the steps of:
providing a calibration fixation target on the display;
prompting the patient to focus on the calibration fixation target for a period of time;
adjusting the position of the marker indicating the patient's point of regard over the calibration fixation target.

11. A method according to claim 1, wherein step (e) comprises changing the brightness of the new target and/or the contrast of the new target relative to the displayed background over a period of time.

12. A method according to claim 11, wherein step (e) further comprises recording the brightness and/or contrast level of the new target at the time of detection.

13. A method according to claim 12, wherein the step of recording the brightness and/or contrast level of the new target at the time of detection comprises accounting for the reaction time of the patient.

14. A method according to claim 1, wherein in step (d), the new target is presented once the marker is moved at least partially over the fixation target.

15. A method according to claim 1, further comprising moving the fixation target and moving the new target with the fixation target to maintain it at a constant position relative to the fixation target, wherein the patient is encouraged to track the movement by maintaining the marker over the fixation target and the new target is only displayed when the marker is over the fixation target or being moved directly towards the new target.

16. A method according to claim 1, further comprising providing the patient with a patient actuated indicator for designating a target as detected, wherein the step of recording the target as detected comprises requiring the patient to actuate the patient actuated indicator once the marker is moved to the target.

17. A non-transitory computer readable medium having instructions for implementing a method for testing a patient's visual field using testing apparatus, the software program comprising:
- (a) instructions for providing a fixation target on a display at a known target position;
- (b) instructions for tracking the patient's direction of gaze using an eye tracker to determine the patient's point of regard on the display;
- (c) instructions for providing a marker on the display indicating the patient's point of regard, where the marker moves with movement of the patient's point of regard;
- (d) instructions for detecting when the marker is moved to the fixation target;
- (e) instructions for providing a new target on the display at a further known target position once the marker is moved to the fixation target;
- (f) instructions for recording the new target as detected if the marker is moved to the new target, the new target then becoming the fixation target;
- (g) instructions for repeating instructions (e) and (f) for further new targets a further known target positions for determining the patient's visual field based on the positions of the new targets that have been detected.

18. Apparatus for testing a patient's visual field, the apparatus comprising:

a display;

an eye tracker for tracking the patient's direction of gaze to determine the patient's point of regard on the display;

a control unit configured to (a) present a fixation target on the display at a known target position; (b) present a marker on the display indicating the patient's point of regard, where the marker moves with movement of the patient's point of regard; and (c) present a new target on the display at a further known target position once the marker is moved to the fixation target;

a memory for recording the new target as detected if the marker is moved to the new target, the new target then becoming the fixation target;

wherein the control unit is further configured to present further new targets at further known target positions and the memory is for recording if the further new targets are detected for determining the patient's visual field based on the positions of the new targets that have been detected.

19. Apparatus according to claim 18, wherein the apparatus comprises a head mounted unit comprising the display and the eye tracker.

20. Apparatus according to claim 18, further comprising a patient actuated indicator for designating a target as detected, wherein the control unit is configured to record targets as detected only when the patient actuated indicator is actuated by the patient once the marker is moved to the target.

* * * * *